(12) United States Patent
Ma et al.

(10) Patent No.: US 12,260,952 B2
(45) Date of Patent: *Mar. 25, 2025

(54) MEDICAL IMAGE PROCESSING METHOD AND SYSTEM AND DATA PROCESSING METHOD

(71) Applicant: Alibaba Group Holding Limited, George Town (KY)

(72) Inventors: Jianqiang Ma, Beijing (CN); Zhe Tang, Beijing (CN); Minfeng Xu, Beijing (CN); Shuangrui Liu, Beijing (CN); Wenchao Guo, Beijing (CN)

(73) Assignee: Alibaba Group Holding Limited (KY)

( * ) Notice: Subject to any disclaimer, the term of this patent is extended or adjusted under 35 U.S.C. 154(b) by 737 days.

This patent is subject to a terminal disclaimer.

(21) Appl. No.: 17/210,250

(22) Filed: Mar. 23, 2021

(65) Prior Publication Data

US 2021/0303935 A1    Sep. 30, 2021

(30) Foreign Application Priority Data

Mar. 31, 2020    (CN) .......................... 202010244937.9

(51) Int. Cl.
*G16H 30/40*    (2018.01)
*G06F 18/241*    (2023.01)
(Continued)

(52) U.S. Cl.
CPC ........... *G16H 30/40* (2018.01); *G06F 18/241* (2023.01); *G06T 7/0012* (2013.01); *G06V 10/25* (2022.01);
(Continued)

(58) Field of Classification Search
None
See application file for complete search history.

(56) References Cited

U.S. PATENT DOCUMENTS 5,769,074 A    6/1998    Barnhill
8,296,247 B2    10/2012    Zhang
(Continued)

FOREIGN PATENT DOCUMENTS

CN    108109152    6/2018
CN    108335282    7/2018
(Continued)

OTHER PUBLICATIONS

Lee et al. "Classification of femur fracture in pelvic X-ray images using meta-learned deep neural network", Sci Rep 10, 13694, Aug. 13, 2020. Retrieved on Jun. 3, 2021. Retrieved from <URL: https://www.nature.com/articles/s41598-020-70660-4> entire document.

*Primary Examiner* — Fan Zhang
(74) *Attorney, Agent, or Firm* — Van Pelt, Yi & James LLP

(57)    ABSTRACT

The present application discloses a method, device, and system for processing a medical image. The method includes obtaining, by one or more processors, a first medical image, wherein the first medical image includes a representation of a target organ, and processing, by the one or more processors, the first medical image based at least in part on a first machine learning model. A classification result associated with the first medical image and a first image of a target region in the first medical image are obtained based at least in part on the processing of the first medical image using the first machine learning model.

18 Claims, 7 Drawing Sheets

(51) Int. Cl.
  *G06T 7/00*    (2017.01)
  *G06V 10/25*   (2022.01)
  *G06V 10/44*   (2022.01)
  *G06V 10/774*  (2022.01)
  *G06V 10/82*   (2022.01)

(52) U.S. Cl.
  CPC .......... *G06V 10/454* (2022.01); *G06V 10/774* (2022.01); *G06V 10/82* (2022.01); *G06T 2207/20081* (2013.01); *G06T 2207/20084* (2013.01); *G06T 2207/30061* (2013.01)

(56) References Cited

U.S. PATENT DOCUMENTS

| | | |
|---|---|---|
| 8,543,519 B2 | 9/2013 | Guyon |
| 9,589,374 B1 | 3/2017 | Gao |
| 9,980,704 B2 | 5/2018 | Gratacös |
| 10,013,757 B2 | 7/2018 | Kim |
| 10,127,659 B2 | 11/2018 | Hsieh |
| 10,140,544 B1 | 11/2018 | Zhao |
| 10,304,193 B1 | 5/2019 | Wang |
| 10,354,171 B2 | 7/2019 | Hsieh |
| 10,430,946 B1 | 10/2019 | Zhou |
| 10,445,462 B2 | 10/2019 | Sorenson |
| 10,452,813 B2 | 10/2019 | Sorenson |
| 10,643,331 B2 | 5/2020 | Ghesu |
| 10,740,901 B2 | 8/2020 | Myronenko |
| 10,825,168 B2 | 11/2020 | Tegzes |
| 2004/0131254 A1 | 7/2004 | Liang |
| 2014/0088415 A1 | 3/2014 | Hielscher |
| 2016/0300351 A1 | 10/2016 | Gazit |
| 2016/0350919 A1 | 12/2016 | Steigauf |
| 2017/0217102 A1* | 8/2017 | Mansi .................... G16H 50/50 |
| 2017/0337682 A1 | 11/2017 | Liao |
| 2018/0028079 A1 | 2/2018 | Gurevich |
| 2018/0253843 A1 | 9/2018 | Gillies |
| 2018/0289336 A1 | 10/2018 | Osawa |
| 2018/0330207 A1 | 11/2018 | Zhou |
| 2019/0110753 A1 | 4/2019 | Zhang |
| 2019/0188870 A1 | 6/2019 | Park |
| 2019/0325621 A1 | 10/2019 | Wang |
| 2020/0058126 A1 | 2/2020 | Wang |
| 2020/0082534 A1 | 3/2020 | Nikolov |
| 2020/0258227 A1 | 8/2020 | Liao |
| 2021/0090738 A1 | 3/2021 | Bates |
| 2022/0148282 A1* | 5/2022 | Takahashi ............. G06V 10/70 |
| 2023/0218169 A1* | 7/2023 | Yang ........................ G06T 5/40 |
| | | 382/128 |

FOREIGN PATENT DOCUMENTS

| | | | |
|---|---|---|---|
| CN | 109074500 | | 12/2018 |
| CN | 109214349 | | 1/2019 |
| CN | 109447169 | | 3/2019 |
| CN | 109886273 | | 6/2019 |
| CN | 110414428 | | 11/2019 |
| CN | 110647926 | | 1/2020 |
| CN | 110706207 | | 1/2020 |
| CN | 110852285 A * | 2/2020 |
| JP | 2018175227 | | 11/2018 |
| KR | 20140028534 | | 3/2014 |
| KR | 20190060606 | | 6/2019 |
| WO | 2020026223 | | 2/2020 |
| WO | 2020044840 | | 3/2020 |
| WO | WO-2021118581 A1 * | 6/2021 | ........... G06T 7/0012 |

* cited by examiner

MEDICAL IMAGE PROCESSING METHOD AND SYSTEM AND DATA PROCESSING METHOD

CROSS REFERENCE TO OTHER APPLICATIONS

This application claims priority to People's Republic of China Patent Application No. 202010244937.9 entitled MEDICAL IMAGE PROCESSING METHOD AND SYSTEM AND DATA PROCESSING METHOD filed Mar. 31, 2020 which is incorporated herein by reference for all purposes.

FIELD OF THE INVENTION

The present application relates to a medical field. Specifically, the present application relates to a medical image processing method and system and a data processing method.

BACKGROUND OF THE INVENTION

Processing of a medical image generally includes using a classification network to obtain a classification result for the medical image, and extracting a lesion region from the medical image using a segmentation network.

However, processing methods for processing medical images generally require a separate training of a classification network and a segmentation network. The classification network is concerned with the features of human organs throughout the medical image and is unable to focus on a lesion region. Accordingly, the classification network has relatively low recognition accuracy (e.g., with respect to accurately recognizing the lesion network). In addition, pixel-level labeling of segmentation data is difficult and relatively little segmentation data exists (e.g., is generated). Thus, the training of a segmentation network using relatively little segmentation data results in lower processing accuracy of the segmentation network.

No effective solution has yet been put forward to address the problems described above.

BRIEF DESCRIPTION OF THE DRAWINGS

Various embodiments of the invention are disclosed in the following detailed description and the accompanying drawings.

The drawings described here are intended to further the understanding of the present application and form a part of the present application. The illustrative embodiments of the present application and the descriptions thereof are intended to explain the present application and do not constitute inappropriate limitation to the present application. Among the drawings.

DETAILED DESCRIPTION

Figure 1:
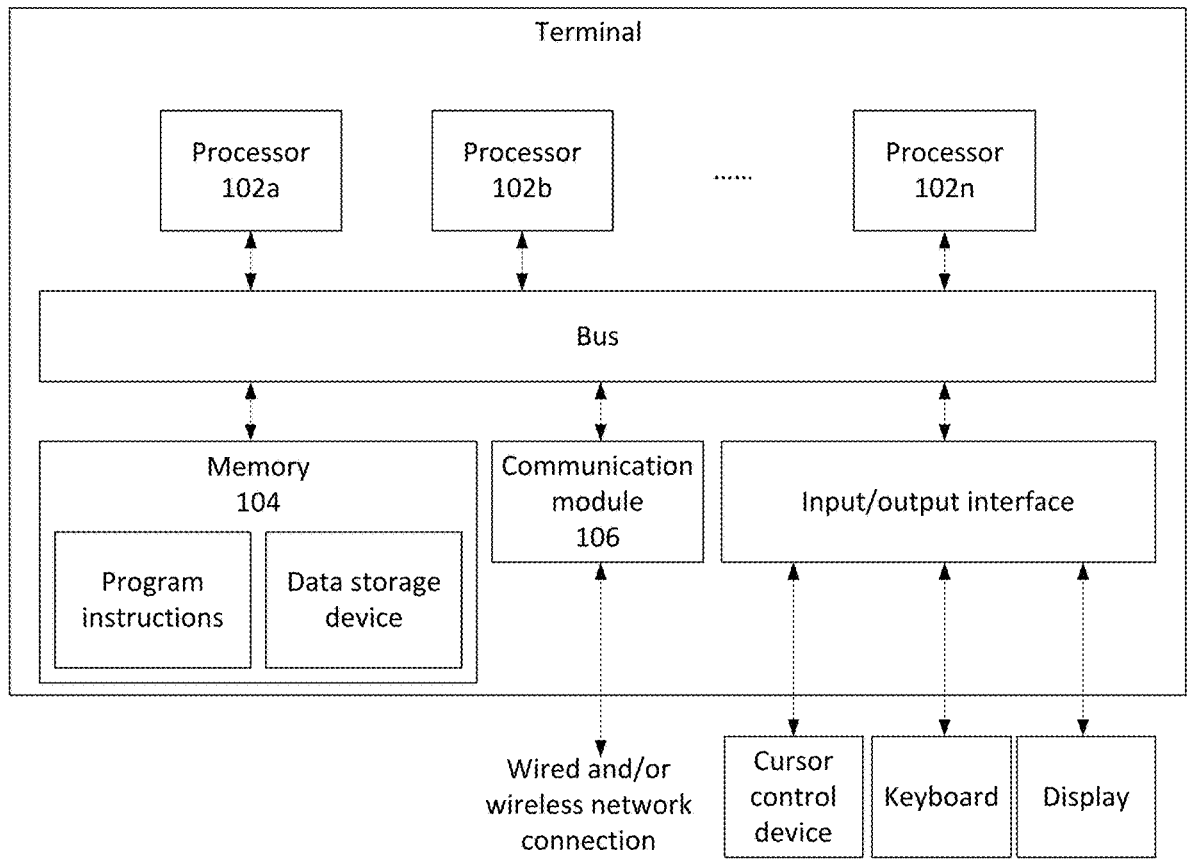
FIG. 1 is a hardware structural block diagram of a computer terminal for implementing a medical image processing method according to various embodiments of the present application.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications, and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

In order to give persons skilled in the art a better understanding of the present application, technical schemes in embodiments of the present application are described clearly and completely in light of the drawings of the embodiments of the present application. Obviously, the embodiments described are merely some of the embodiments of the present application and are not all the embodiments. So long as no additional creative effort is expended, all other embodiments that are obtained by persons with ordinary skill in the art on the basis of embodiments in the present application shall fall within the scope of protection of the present application.

Please understand that the terms "first," "second," etc. in the description, claims, and drawings of the present application are used to differentiate similar objects and are not necessarily used to describe their particular sequence or order. It should be understood that data used in this way may be switched as appropriate. Thus, embodiments of the present application described herein can be implemented in sequences other than those shown or described herein. In addition, the terms "comprise" and "have" and the variations thereof are meant to be non-exclusive. For example, a process, method, system, product, or device containing a series of steps or units need not be limited to those steps or units that are clearly listed, but may comprise other steps or units that are not clearly listed or that are intrinsic to these processes, methods, products, or devices.

As used herein, a "terminal" generally refers to a device comprising one or more processors. A terminal can be a device used (e.g., by a user) within a network system and used to communicate with one or more servers. According to various embodiments of the present disclosure, a terminal includes components that support communication functionality. For example, a terminal can be a smart phone, a server, a machine of shared power banks, information centers (such as one or more services providing information such as traffic or weather, etc.), a tablet device, a mobile phone, a video phone, an e-book reader, a desktop computer, a laptop computer, a netbook computer, a personal computer, a Personal Digital Assistant (PDA), a Portable Multimedia Player (PMP), a mobile medical device, a camera, a wearable device (e.g., a Head-Mounted Device (HMD), electronic clothes, electronic braces, an electronic necklace, an electronic accessory, an electronic tattoo, or a smart watch), a kiosk such as a vending machine, a smart home appliance, vehicle-mounted mobile stations, or the like. A terminal can run various operating systems.

As used herein, a client refers to a terminal that communicates with a server. The client may be implemented on a terminal via one or more applications running on the terminal. For example, the client may refer to a mobile terminal that communicates with the server via one or more networks. The mobile terminal can run an application (e.g., a client application) that communicates with the server in connection with performing one or more operations at the mobile terminal. The client can communicate information to the server. In some embodiments, the information communicated from the client to the server includes one or more requests, etc. The client may also receive information from the server (e.g., via communication with one or more networks). In some embodiments, the information that the client receives from the server includes information pertaining to an image analysis performed with respect to an image such as a medical image. For example, the information pertaining to an image analysis includes a classification of the image and/or an identification of target data that is determined based at least in part on the image (e.g., the medical image).

As used herein, reinforcement learning refers to a type of learning capable of taking environment-based actions to obtain expected benefits.

As used herein, an encoder-decoder model refers to a model framework in deep learning. The encoder-decoder model can be divided into two parts: an encoder network and a decoder network.

As used herein, UNet refers to a convolutional neural network. The UNet can be divided into two parts: a first half that is used in connection with feature extraction; and a second half that is used in connection with upsampling.

As used herein, a pyramid scene parsing network (PSP-Net) refers to a network that aggregates context information based on different regions to exploit global context information capabilities.

As used herein, DeepLabV3+(DeepLab) refers to a method of combining deep convolutional neural networks (DCNNs) and probabilistic graphical models (DenseCRFs). DeepLab puts forward an atrous spatial pyramid pooling module. The atrous spatial pyramid pooling module is used in connection with exploring multi-scale convolutional features and encoding global backgrounds based on image layers to obtain features.

As used herein, resnext refers to a homogeneous neural network. Resnext comprises multiple branches using the same topological structure. The number of channels of the feature map generated by each branch is n.

As used herein, an Atrous Spatial Pyramid Pooling (ASPP) structure refers to a module that uses multi-scale information to further reinforce segmentation results.

As used herein, rigid transformation refers to a transformation of an object in which only a position (translation transformation) and direction (rotation transformation) of the object is changed, but the shape does not change.

As used herein, affine transformation refers to a transformation involving any inclination of a graphic and any expansion or contraction of a graphic in two directions.

According to various embodiments, a medical image is processed in connection with providing information that classifies the medical image. The medical image may be processed to obtain target data such as information pertaining to a particular region of the medical image. In some embodiments, the processing of the medical image includes extracting one or more lesion regions and/or organ regions (e.g., human organ regions). The extraction of the one or more lesion regions and/or organ regions may be based at least in part on a segmentation of the medical image and quantitative analysis of the medical image or a segmented part of the medical image. According to various embodiments, the processing of the medical image may facilitate accurate diagnosis of a patient (e.g., determination of a medical condition of the patient) via at least medical imaging. A physician or other medical professional may use the results of the processing of the medical image in connection with diagnosing a patient and/or determining a treatment for an identified medical condition. For example, the quantitative results may help the physician to determine the medical condition of the patient and to provide appropriate treatment based on the medical condition.

In current medical imaging technologies, medical image type identification and target segmentation network models are mutually independent. The current medical imaging technologies generally require training of two independent networks: a classification network and a segmentation network. Each of the networks are further discussed below.

The classification network is primarily used for determining the category of a medical image, and the segmentation network is used for extracting lesion regions. However, current technologies do not take into account the fact that classification networks and segmentation networks are unified in terms of medical image texture features. The primary basis on which a classification network makes a category assessment is generally the texture features of the lesion region. However, a pure classification network has difficulty focusing (e.g., identifying) on a lesion region. As a result, a trained model according to current medical imaging technologies (e.g., using a pure classification network to identify a lesion region) has relatively low recognition accuracy.

A segmentation network is generally implemented on the basis of two-dimensional neural network images. However, because a segmentation network does not consider three-dimensional spatial relationships, the segmentation precision is relatively low.

In addition, according to current medical imaging and diagnostic technologies, during follow-up, a physician is generally required to view separate medical images of a patient from different time periods and will need to analyze how the lesion region has changed. The overall process is relatively time-consuming and relatively inefficient.

In order to resolve the problems described above, a medical image processing method is provided according to an embodiment of the present application. Please note that the steps depicted in the flowcharts in the drawings can be executed in a computer system, such as a group of computers capable of executing instructions. Moreover, although logical sequences are depicted in the flowcharts, the steps that are depicted or described may, in some situations, be executed in sequences other than those described here.

FIG. 1 is a hardware structural block diagram of a computer terminal for implementing a medical image processing method according to various embodiments of the present application.

Figure 2:
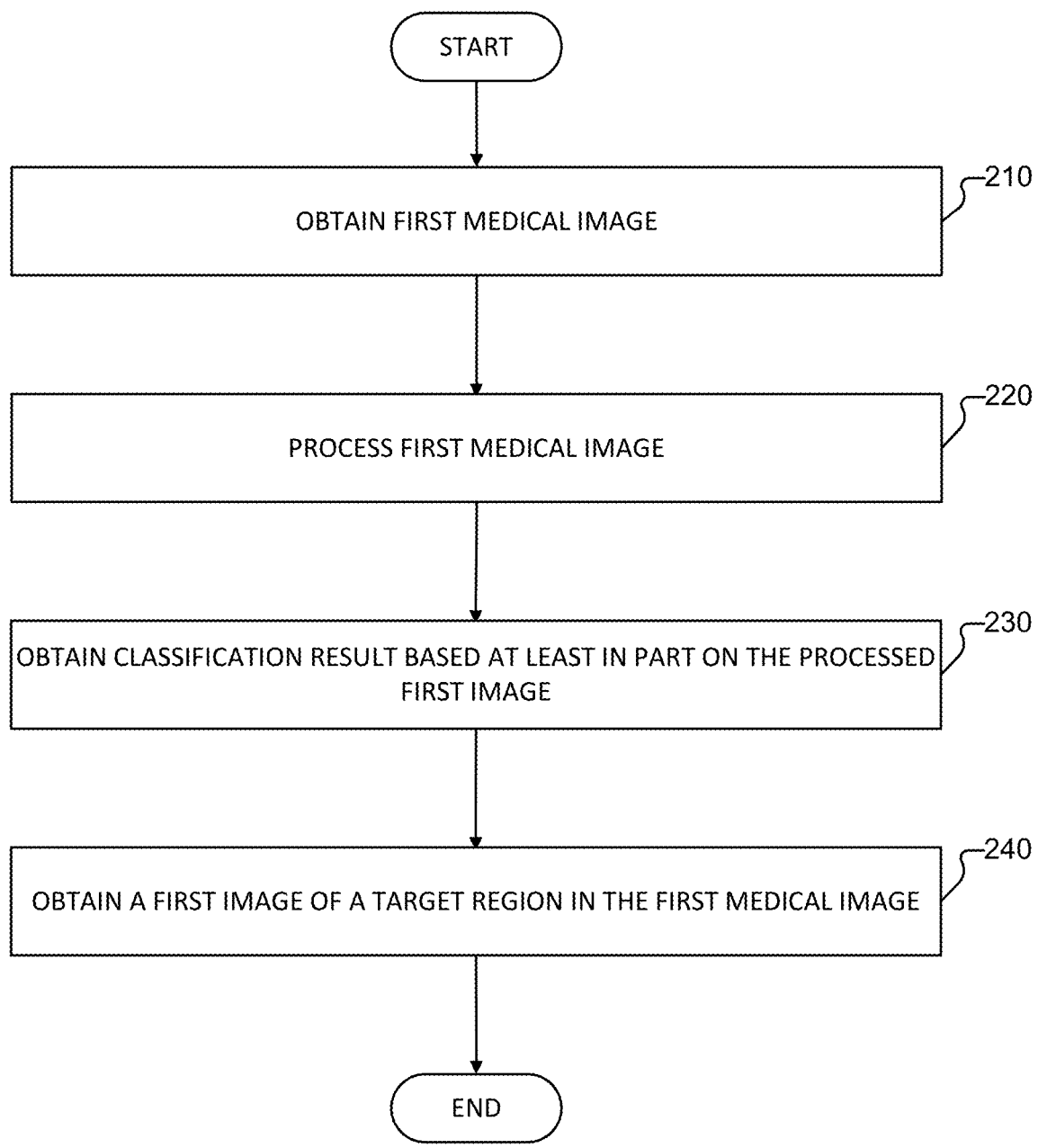
FIG. 2 is a flowchart of a method for processing a medical image according to various embodiments of the present application.
Figure 3:
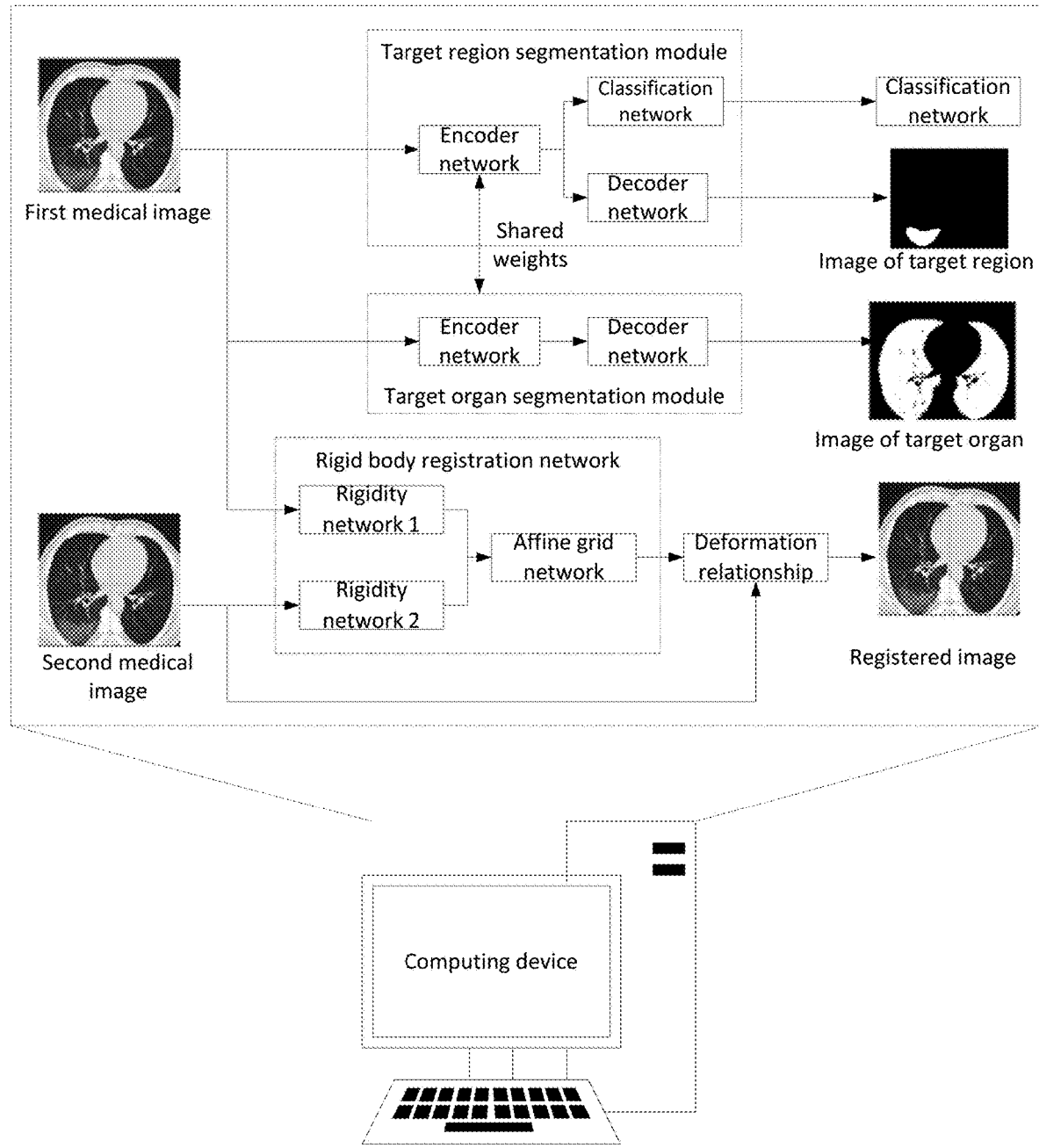
FIG. 3 is a flowchart of a method for processing a medical image according to various embodiments of the present application.
Figure 4:
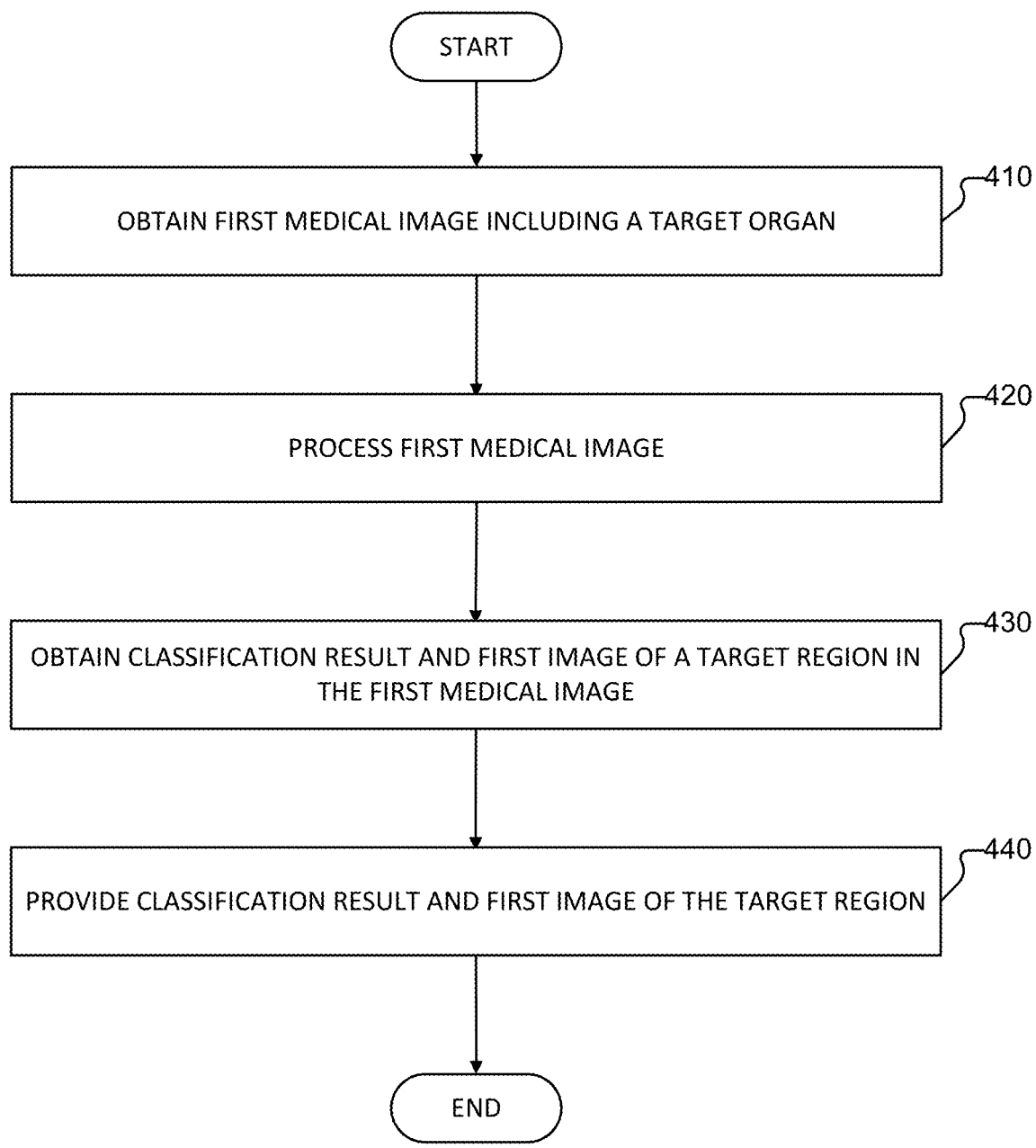
FIG. 4 is a flowchart of a method for processing a medical image according to various embodiments of the present application.
Figure 5:
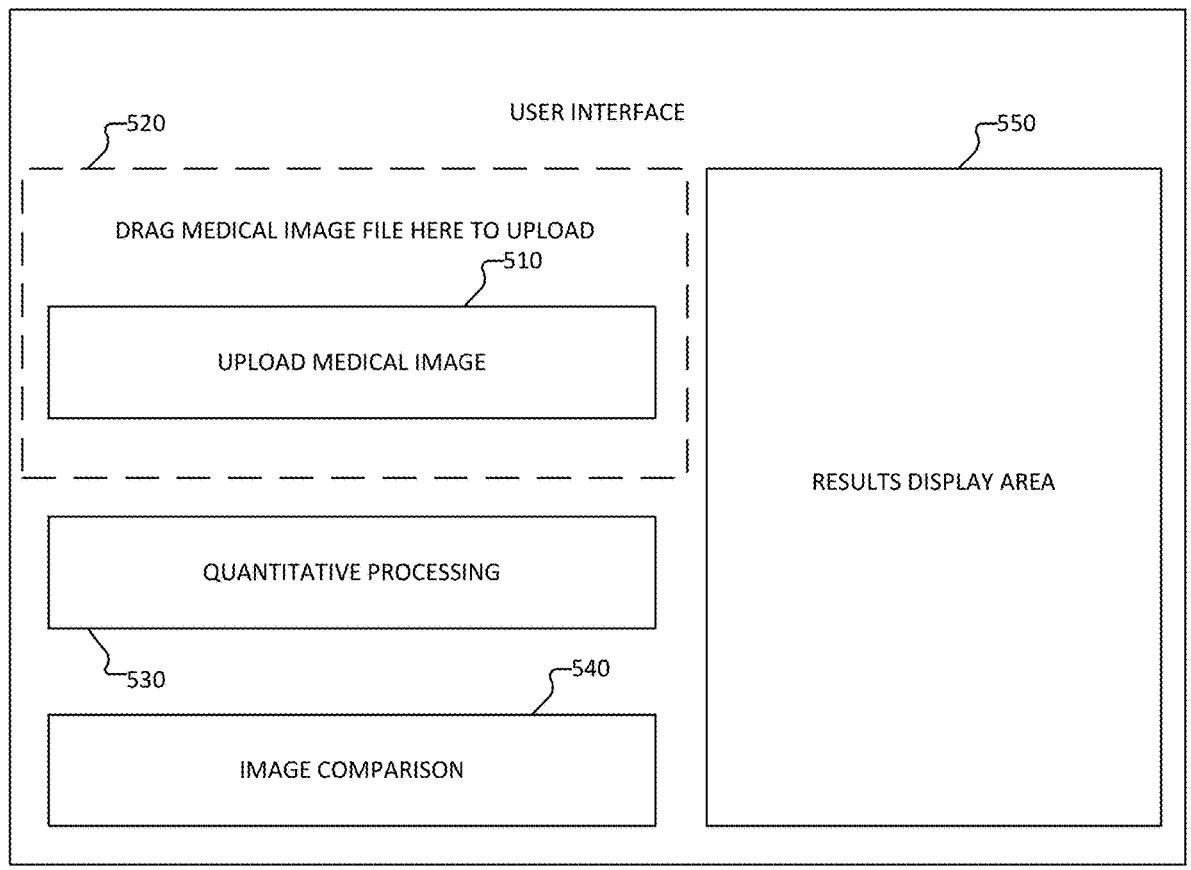
FIG. 5 is a diagram of an interface used in connection with processing a medical image according to various embodiments of the present application.
Figure 6:
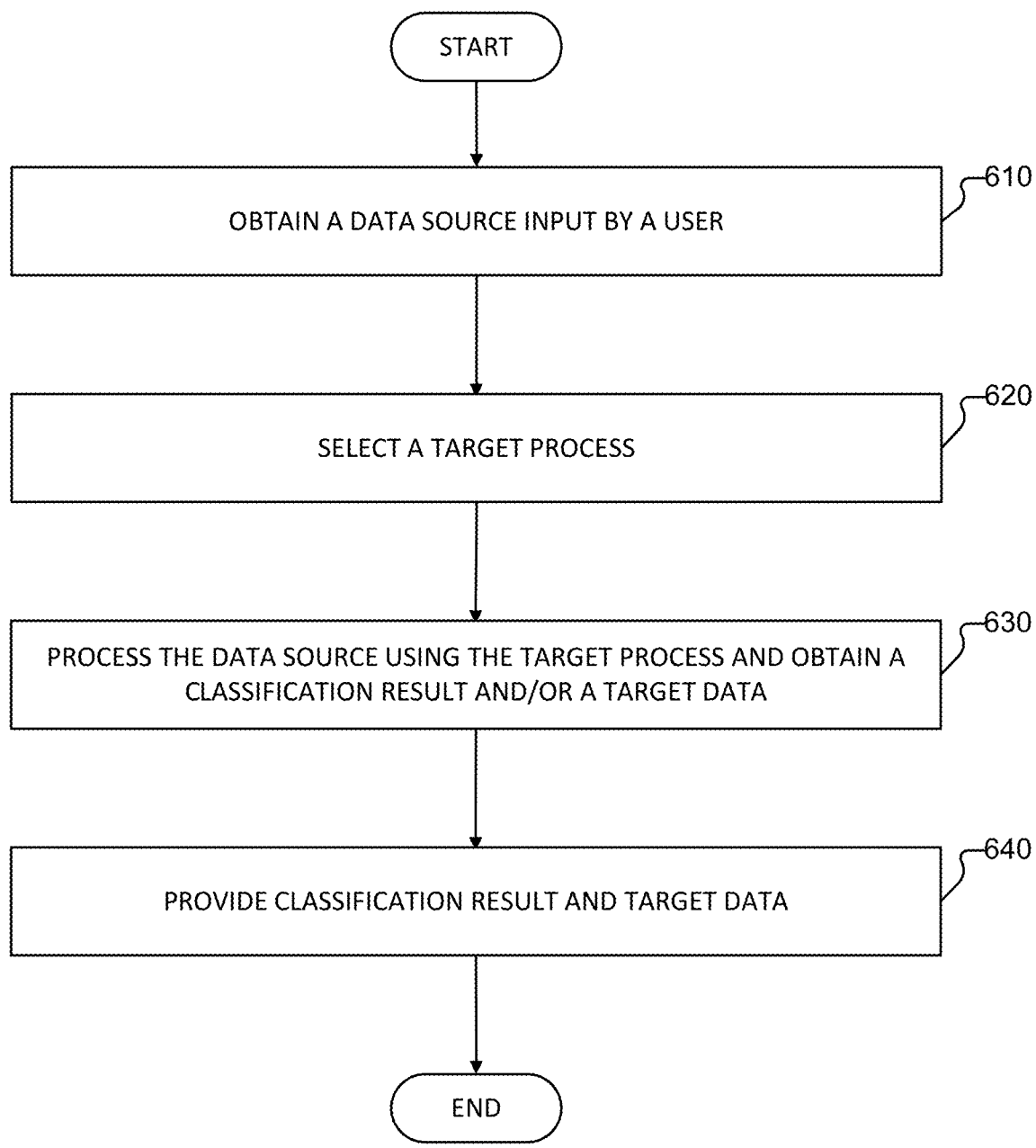
FIG. 6 is a flowchart of a method for processing a medical image according to various embodiments of the present application.
Figure 7:
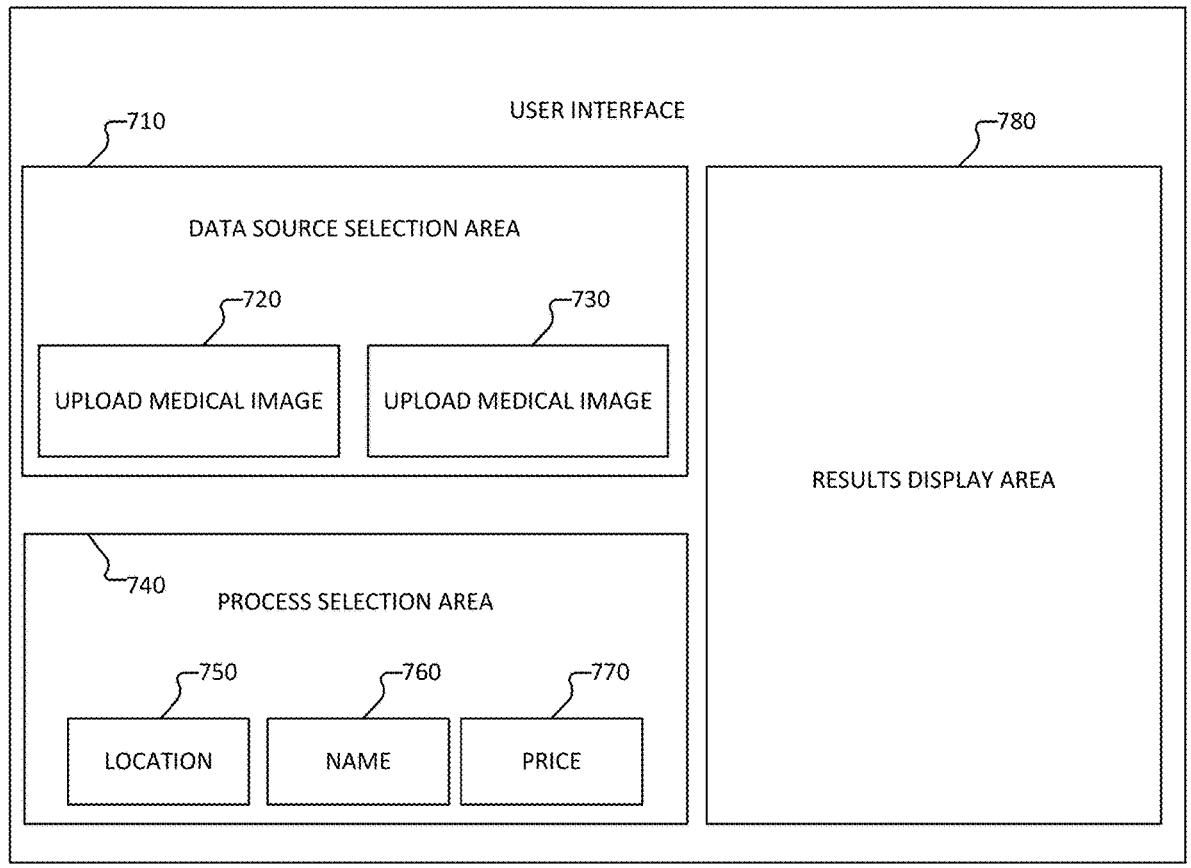
FIG. 7 is a diagram of an interface used in connection with processing a medical image according to various embodiments of the present application.

According to various embodiments, terminal 100 implements at least part of process 200 of FIG. 2, process 300 of FIG. 3, process 400 of FIG. 4, interface 500 of FIG. 5, process 600 of FIG. 6, and/or interface 700 of FIG. 7.

As shown in FIG. 1, terminal 100 may comprise one or more processors 102 (indicated by 102a, 102b, . . . , 102n in the drawing). Processors 102 may include, but are not limited to, processing means such as microprocessors (MCU) or programmable logic devices (FPGA). Terminal 100 may include memory 104 for storing data (e.g., information, executable instructions, medical information, data pertaining to a quantitative analysis of the medical information, etc.), and a communication module 106 for communication functions. Terminal 100 may include a display device, input/output interfaces (I/O interfaces), a universal serial bus (USB) port (may be included as a port among bus ports), a network interface, a power supply, and/or a camera. The terminal 100 of FIG. 1 is illustrative and does not impose restrictions on the structures of the electronic devices described above. For example, terminal 100 may further comprise more or fewer components than are shown in FIG. 1 or have a configuration different from the one shown in FIG. 1.

Please note that the one or more processors 102 and/or other data processing circuits may generally be referred to as "data processing circuits" in this document. All or part of the data processing circuits may be embodied as software, hardware, firmware, or any combination thereof. In addition, a data processing circuit can be a single, independent processing module or any of the other components that are fully or partially integrated with the terminal 100. The data processing circuits of various embodiments of the present application are used as a kind of processor control (e.g., selection of variable resistance terminal paths for connecting to interfaces).

Memory 104 may be used to store software programs and modules of the application software (e.g., program instructions/data storage means corresponding to a method for processing a medical image according to various embodiments of the present application). In connection with running software programs and modules stored in memory 104, processor 102 executes various function applications and data processing, (e.g., the processor implements the method for processing a medical image according to various embodiments of the present application). Memory 104 may comprise high-speed random access memory. Memory 104 comprises non-volatile memory, such as one or more magnetic storage devices, flash memory, or other non-volatile solid-state memory. In some embodiments, memory 104 comprises a memory that is remotely disposed relative to processor 102. Such remote memory may be connected to the terminal 100 via one or more networks. Examples of the network described above include, but are not limited to, the Internet, corporate intranets, local area networks, mobile communication networks, and combinations thereof.

Communication module 106 may be configured to receive and/or send information such as a medical image, information pertaining to a medical image, etc. via a network (e.g., a wired network and/or a wireless network). Examples of the network include wireless networks such as Bluetooth®, WiFi, cellular networks, wireless personal area networks (WPANs), wireless local area networks (WLAN), wireless wide area networks (WWANs), wireless metropolitan area networks (WMAN), etc. In some embodiments, communication module 106 comprises a network interface controller (NIC), which may connect to other networks via a base station or the like and thereby communicate with the Internet. In some embodiments, communication module 106 comprises a radio frequency (RF) module, which is configured to communicate with the Internet wirelessly.

The display device can, for example, be a touch-screen liquid crystal display (LCD). The liquid crystal display may enable the user to interact with the user interface of the terminal 100 (e.g., a mobile terminal). In some embodiments, the display device is controlled to display a user interface with which information pertaining to a medical image and/or a quantitative analysis of a medical image is provided (e.g., a target region, etc.). The display device can be integrated into terminal 100 or operatively connected to terminal 100.

According to various embodiments, terminal 100 includes hardware components (e.g., including circuits), software components (e.g., including computer code stored on computer-readable media), or combinations of both hardware components and software components. Please note that FIG. 1 is merely one example of a particular, specific embodiment with the purpose of presenting the types of components that may exist in the aforesaid computer device (or mobile device).

Various embodiments provide a method for processing a medical image. In some embodiments, a medical image is processed in connection with performing a quantitative analysis on the medical image. For example, the medical image may be processed to determine one or more target regions (e.g., a lesion region and/or an organ region). Information pertaining to the target region may be provided to a user via a user interface on a terminal.

FIG. 2 is a flowchart of a method for processing a medical image according to various embodiments of the present application.

According to various embodiments, process 200 is implemented by terminal 100 of FIG. 1. Interface 500 of FIG. 5 and/or interface 700 of FIG. 7 may be implemented in connection with process 200.

At 210, a first medical image is obtained. In some embodiments, the obtaining the first medical image includes receiving the first medical image via an upload by a user. The first medical image may be obtained from diagnostic equipment (e.g., an x-ray machine, a magnetic resonance imaging machine, a computerized tomography scan, etc.). The first medical image may be obtained from a data storage such as a server (e.g., a server that stores a database of medical images).

In some embodiments, the first medical image comprises a representation of a target organ. The target organ may be identified by a computer and/or an indication of the target organ may be provided by a user (e.g., via a user interface provided on a terminal). As an example, the target organ is a human organ in the body of a patient (e.g., a human, an animal, a living being, etc.). Examples of a target organ include a brain, a heart, a lung, etc.

In some embodiments, the first medical image corresponds to the image of a target organ obtained with a medical imaging technology. The first medical image may be obtained directly from medical imaging technology or indirectly via accessing a storage on which the first medical image is stored (e.g., a storage on which the medical imaging technology stores the first medical image). As an example, the medical imaging technology may be, but is not limited to, X-rays, gamma rays, nuclear magnetic resonance, or ultrasound. Various medical imaging technologies may be used for capturing medical images corresponding to different target organs. The present application imposes no specific restrictions in this regard. Embodiments of the present application are explained using the example of a target organ that is a lung and a first medical image that is a CT (computed tomography) image.

At 220, the first medical image is processed. According to various embodiments, the processing of the first medical image includes using a first machine learning model to process the first medical image. The first machine learning model may process the first medical image in connection with generating a classification result pertaining to the first medical image.

At 230, a classification result is obtained. In some embodiments, the classification result is obtained based at least in part on the processed first image. In some embodiments, the classification result is an output of the first machine learning model. The classification result may be stored in a data storage such as the data storage on which the first medical image is stored, etc. For example, the classification result may be stored on a network storage (e.g., in a database).

At 240, a first image of a target region is obtained. In some embodiments, the first image of the target region is obtained based at least in part on the processed first image. In some embodiments, the first image of the target region is an output of the first machine learning model. The first image of the target region may be stored in a data storage such as the data storage on which the first medical image is stored, etc. For example, the first image of the target region may be stored on a network storage (e.g., in a database).

According to various embodiments, the first machine learning model is configured to obtain the first medical image, input the first medical image into an encoder network, obtain feature information pertaining to a target region, and separately input the feature information about the target region into a classification network and a decoder network to obtain the classification result and the first image.

According to various embodiments, the first machine learning model is used to process the first medical image and obtain a classification result for the first medical image and a first image of a target region in the first medical image. The first machine learning model comprises obtaining the first medical image, inputting the first medical image into an encoder network, obtaining feature information about the target region, and separately inputting the feature information about the target region into a classification network and a decoder network to obtain the classification result and the first image (e.g., the classification result is obtained from the classification network and the first image of the target region is obtained from the decoder network). In some embodiments, an encoder network comprises a convolutional neural network.

According to various embodiments, the first machine learning model is a trained model, or a reinforcement learning model. In embodiments of the present application, the example of a trained model is used for the purpose of illustration. The first machine learning model may use an "encoder-decoder" structure and may connect after the encoder network to a classification network which is parallel to the decoder network. For example, the network model may employ an "encoder-decoder" structure and the output from the encoder network may correspond to an input to both the classification network and the decoder network, such that the classification network and the decoder network operate in parallel. As another example, the output from the encoder network may be operatively connected to an input to both the classification network and the decoder network, such that the classification network and the decoder network operate in parallel (e.g., the output from the encoder may be input to another processing module before being input to the classification network and/or the decoder network). In some embodiments, one or more of the encoder network and the decoder network use three-dimensional convolutional layers. As an example, both the encoder network and the decoder network use three-dimensional convolutional layers. For example, the first machine learning model may be a three-dimensional network model. In some embodiments, the encoder network employs a resnext50 network architecture. The decoder network may include an ASPP structure and upsampling layers, and the classification network may include a series of convolutional layers and global pooling layers. However, the encoder network, the decoder network, and the classification network are not limited to the foregoing.

According to various embodiments, the classification results (e.g., obtained from processing the first medical image) comprise a set of one or more classifications. The set of one or more classifications may be configured by a user (e.g., the user that uploads the medical image), an administrator, etc. In some embodiments, the set of one or more classifications is preset based at least in part on a mapping of a set of one or more classifications to a type of medical image, a type of target organ, or a type of analysis/diagnosis that is desired (which may be selected by the user via an input to a user interface). In some embodiments, classification results may comprise classification results set in advance for the target organ (e.g., a mapping of classification results to target organs is pre-stored). As an example, in the case of a medical image of a lung, the classification results may include, but are not limited to: diseased lung image, normal lung image, etc. The classification results (e.g., the set of one or more classifications associated with a particular target organ) can be according to actual need, preferences, etc.

According to various embodiments, the target region corresponds to the region (of the corresponding organ) of possible pathologic change in the target organ. In some embodiments, the target region corresponds to a specific region that is to be extracted from the target organ. The target region can be set by a user in connection with determining (e.g., defining) parameters of the processing of the medical image.

According to various embodiments, a joint, multi-task classification and segmentation network model is built (e.g., defined) in advance. For example, such a model may be built in advance of the processing or obtaining of the first medical image. The model may be updated in connection with the processing of a plurality of medical images (e.g., as each medical image that is processed by the model, the model may be continually improved/updated). The network model may employ an "encoder-decoder" structure and the output from the encoder network may correspond to an input to both the classification network and the decoder network, such that the classification network and the decoder network operate in parallel. In some embodiments, in response to the first medical image being obtained, the first medical image is input into the first machine learning model (e.g., the joint, multi-task classification and segmentation network). The appropriate classification result may be output through the classification network branch, and an image of the target region (e.g., the first image of the target region) may be output through the decoder network branch.

According to various embodiments, in response to obtaining a first medical image, a first machine learning model is used to process the first medical image and to obtain a classification result and a first image of the target region, thereby achieving a goal of image classification and area segmentation. The classification result and the first image may be obtained simultaneously (e.g., contemporaneously). In some embodiments, the classification network and the segmentation network are combined, thereby enabling the classification network to focus on the target region in the classification process. The use of a combination of a classification network and a segmentation network improves processing accuracy and efficiency and thus solves the technical problem of low accuracy of medical image processing in the related art.

According to various embodiments, the first machine learning model is trained before processing the first medical image. The first machine learning model can be updated in response to the first medical image being processed. In some embodiments, process 200 further includes obtaining a plurality of training samples (or a plurality of types of training samples) and training the first machine learning model based at least in part on the plurality of training samples. For example, process 200 may include obtaining multiple first training samples and multiple second training samples. Each first training sample may include a medical image containing the target organ, a classification label for the medical image, and label information for a target region in the medical image, and each second training sample may include a medical image containing the target organ and the classification label for the medical image. Process 200 may further include training the first machine learning model. The training of the first machine learning model may include alternating between use of multiple first training samples and multiple second training samples to train a preset model and obtain a first machine learning model (or an updated first machine learning model). According to various embodiments, the first training samples include classification label(s), and the second training samples include the classification label(s) and the target region labels.

Medical images in first training data (e.g., first training samples) and second training data (e.g., second training samples) may be masked data collected through various channels, such as hospitals and picture archiving and communication systems (PACS) companies to enhance the training results. Each medical image may be manually assigned a classification label in accordance with the different medical conditions, and target regions may likewise be labeled.

Because labelling of pixel-level target regions is relatively difficult, a quantity of training samples that include target region markings is relatively limited. According to various embodiments, in connection with implementing model training and improving processing accuracy, the training data may be divided into two types of data. One type of data corresponds to data that only includes the classification label(s) (e.g., the aforementioned first training data or first training samples), and the other type of data corresponds to data that includes the classification label and the target region labels (e.g., the aforementioned second training data or second training samples). In some embodiments, the model (e.g., the first machine learning model) is trained according to an iterative process.

According to various embodiments, different loss functions are used to conduct classification network and decoder network training. For example, training the model may include alternating between/among different loss functions in connection with processing the classification network and the decoder network. With the iterative training approach, all labeled data may be used, and image classification and region segmentation may mutually promote extraction of more meaningful features, thus improving classification accuracy and segmentation precision. In addition, an iterative and/or alternating training process (of training the model) may cause the classification network to focus on the target region and may increase the explanatory value of the classification result.

FIG. 3 is a flowchart of a method for processing a medical image according to various embodiments of the present application.

According to various embodiments, process 300 is implemented by terminal 100 of FIG. 1. Interface 500 of FIG. 5 and/or interface 700 of FIG. 7 may be implemented in connection with process 300.

Process 300 is described in the context of a CT image of a lung as an example. As illustrated in FIG. 3, in response to obtaining a patient CT image, the corresponding medical image is input into the target region segmentation module. The segmentation module may comprise an encoder network, a classification network, and a decoder network. The classification network and the decoder network may be connected in parallel to the encoder network (e.g., connected to an output of the encoder network). In some embodiments, the encoder network extracts and processes the medical image. For example, the encoder network extracts target region features, and the target region features are input to the classification network and/or the decoder network. In response to receiving the target region features, the classification network processes the target region features and obtains an image classification result. In parallel with the processing by the classification network (e.g., at the same time), the decoder network processes the target region features and extracts an image of the target region (e.g., a first image of the target region). The image of the target region can be stored and/or provided to a user via a user interface. For example, a physician or care provider can view information pertaining to outputs from the classification network and/or the decoder network and can quickly determine the condition of the patient, thereby allowing the physician or care provider to perform early intervention and treatment to prevent the condition from becoming serious or even critical, thus lowering the fatality rate.

According to various embodiments, after obtaining a first image of the target region in the first medical image, the method further comprises: using a second machine learning model to process the first medical image and obtain a second image of the target organ. The second machine learning model includes obtaining the first medical image, inputting the first medical image into a target organ segmentation module, and obtaining an image of the target organ. In some embodiments, the target organ segmentation module processes the first medical image, including inputting the first medical image into an encoder network, obtaining feature information pertaining to the target organ, and inputting the feature information pertaining to the target organ into a decoder network to obtain the second image and to obtain a first proportion of the target region in the target organ based at least in part on the first medical image and the second image.

In some embodiments, quantitative analysis is performed with respect to the target region. Results of the quantitative analysis may be provided to a physician or care provider. For example, the results may be provided via a user interface (e.g., displayed on a display module). In some embodiments, the quantitative analysis includes or is provided with corresponding recommendations for adopting a corresponding treatment regimen. The aforementioned first proportion may be the size of the target region as a proportion of the target organ (e.g., a ratio of the size of the target region to the size of the target organ). Various other proportions may be determined based on the target region relative to the target organ (e.g., using one or more other characteristics such as length, volume, mass, color, etc.).

Low segmentation precision of schemes according to the related art results in inaccurate segmentation of the target region and the target organ region. Relatively accurate segmentation results are unobtainable using current segmentation techniques. To solve the problem described above, various embodiments implement a first machine learning model and a second machine learning model. Similar to the first machine learning model, the second machine learning model may be a trained model or a reinforcement learning model. For illustrative purposes, an example of a trained model is described herein. A trained model and/or a reinforcement learning model may employ an "encoder-decoder" structure. The "encoder-decoder" structure may be obtained by modifying common networks such as UNet, PSPNet, or DeepLabV3+. In some embodiments, the encoder network and decoder network in the second machine learning model use three-dimensional convolutional layers. The first machine learning model and the second machine learning model may thus become three-dimensional networks.

According to various embodiments, because the same medical images are input into the two models (e.g., first machine learning model and second machine learning model), a similarity with respect to extraction of the target region and the organ region is implemented. Accordingly, the encoder network in the second machine learning model and the encoder network in the first machine learning model may share weighting parameters and thus achieve accelerated network training. For example, less processing resources and/or time is used to collectively train the first machine learning model and second machine learning model.

According to various embodiments, a first machine learning model with a joint, multi-task classification and segmentation network and a second machine learning model with a segmentation network may be built (e.g., determined/trained, etc.) before the medical image is obtained. The two models may employ an "encoder-decoder" structure. The two models may have a parallel connection to a classification network following the first machine learning model encoder network (e.g., the encoder network of the first machine learning model may have an input that is input to a classification network of the first model and a classification network of the second machine learning model). According to various embodiments, in response to obtaining the first medical image, the first medical image is input into the first machine learning model and the second machine learning model. The target region may be extracted by the decoder network of the first machine learning model, and the target organ region may be extracted by the decoder network of the second machine learning model. Target region quantification results can be further obtained by calculating the ratio between predetermined characteristics of the two regions, such as a ratio between a size of the target region and the target organ region.

Continuing to use a CT image of a lung as an example, the following provides a detailed description of various embodiments of the present application in view of FIG. 3. As illustrated in FIG. 3, following each acquisition of a patient CT image, the image may be input into a target region segmentation module and a target organ segmentation module. The target region segmentation module and the target organ segmentation module separately process the image (e.g., in parallel) and separately extract the lesion region and the lung region of the lung of the corresponding patient. The system may calculate the size ratio between the lesion region and the lung region in connection with obtaining the quantitative result of the size of the lesion region within the lung. The quantitative results may assist the physician or care provider to quickly and accurately determine the condition of the patient, and to provide appropriate treatment based on the condition.

In some embodiments, the method further includes obtaining a second medical image comprising a target organ; using a first machine learning model to process the second medical image and to obtain a third image of the target region in the second medical image; using the second machine learning model to process the second medical image and to obtain a fourth image of the target organ; and obtaining a second proportion of the target region in the target organ based at least in part on the third image and the fourth image.

During the treatment process, the patient may seek regular follow-ups to determine how the condition of the patent has changed. However, current patient follow-up analysis is carried out entirely through the observations by the physician or care provider. The physician needs to individually view and find the lesion region in medical images from different periods of time and analyze changes in the lesion region. A physician often needs from 10 to 15 minutes to observe a medical image and spends even more time when simultaneously observing multiple medical images. The result is relatively low efficiency and relatively low accuracy.

Various embodiments solve the problem described above and facilitate physician evaluations of treatment effectiveness based at least in part on processing the medical images corresponding to the patient using a same method (e.g., to read/obtain the second medical image of the patient and to process the second image using the same method that was used in connection with processing the first medical image). The second medical image may be processed separately using the first machine learning model and the second machine learning model to obtain the target region and target organ region in the second medical image. The second proportion for the target region may be determined based at least in part on calculating the ratio between the sizes of the two regions. The physician can thus quickly determine the quantitative result for the target region. This saves the physician a large amount of image-reading time, lowers labor costs, and increases efficiency. In some embodiments, comparative values contrasting the first medical image and the second image are computed and/or provided to the user (e.g., the physician or care provider). The computation and/or presentation of the comparative values provides the user with a more efficient analysis or comparison between the first medical image and the second medical image, and reduces the likelihood of human error. In some embodiments, qualitative and/or quantities information pertaining to trends over a set of medical images for a patient is determined and/or provided to the user. Accordingly, the user may quickly assess the condition of the patient, the effectiveness of a current treatment, and/or how the condition has changed over time.

In some embodiments, to further save on processing time, the medical image and the target region proportion are stored after each processing of a medical image, thus making it possible to obtain the second proportion and the second medical image. The medical image, the target region, the target organ region, and/or the target region proportion may be stored in association with the patient (e.g., in a manner that is accessible via the medical chart or electronic medical record corresponding to the patient).

In some embodiments, the method for processing the medical image includes, after obtaining a second medical image including the target organ, using a third machine learning model to process the first medical image and the second medical image and to obtain the deformation relationship between the first medical image and the second medical image. The third machine learning model may include obtaining the first medical image and the second medical image, and inputting the first medical image and the second medical image separately into a plurality of rigidity networks (e.g., two rigidity networks). The rigidity networks may process the first medical images and the second medical images, including obtaining a first rigid body parameter of the first medical image and a second rigid body parameter of the second medical image. In response to obtaining the first rigid body parameter and the second rigid body parameter, the first rigid body parameter and the second rigid body parameter may be input into an affine grid network in connection with obtaining the deformation relationship (e.g., one or more values pertaining to a change between the second medical image and the first medical image, and/or the second rigid parameter and the first rigid parameter). In some embodiments, the processing of the medical image includes processing the second medical image based at least in part on the deformation relationship to obtain a registered image corresponding to the second medical image. The first machine learning model and the second machine learning model may be separately used to process the registered image and to obtain a third image (e.g., obtained by the first machine learning model) and a fourth image (e.g., obtained by the second machine learning model).

Medical images acquired at different times are often different for the same patient. As a result, the target regions obtained by segmentation differ. The physician thus cannot visually analyze target regions from different times and thereby determine how the condition of the patient has changed.

To solve the problem described above, various embodiments include a registration network (e.g., the third machine learning model described above). Medical images from different time periods may be input into this network, and the medical images from different time periods may be processed by a rigidity network having the same structure so as to determine the rigid body parameters of the medical images. The rigid body parameters may be processed using an affine grid network to obtain a deformation relationship between a set of medical images. For example, the processing of the rigid body parameters based at least in part on the use of an affine grid network includes determining deformation fields between the medical images (e.g., the deformation relationship between the medical images).

In some embodiments, after obtaining the first medical image, a second medical image (e.g., of the patient) is obtained. The second medical image may correspond to a same organ of a same patient as the first medical image. The first medical image and the second medical image may be captured at different times (e.g., a first medical image may be captured before a patient begins treatment, and a second medical image may be captured after treatment has initiated). A third machine learning model may be used to process the first medical image and the second medical image to obtain the deformation relationship between the two medical images. Information pertaining to the deformation relationship between the first medical image and the second medical image may include an indication of an extent and/or type of change or difference between the first medical image and the second medical image. According to various embodiments, in response to determining the deformation relationship between the first medical image and the second medical image, the second medical image is processed based at least in part on the deformation relationship to obtain a registered image.

Continuing to use a CT image of a lung as an example, the following provides a detailed description of various embodiments of the present application in view of FIG. 3. As illustrated in FIG. 3, following each acquisition of a patient CT image, another CT image of the patient may be obtained, and the two CT images may be input into a rigid body registration network. A module for the rigid body registration network (e.g., to which the two CT images are input) processes the two CT images to obtain the deformation relationship between the two CT images. The second medical image (e.g., the second CT image) may be processed based at least in part on the deformation relationship. A registration network corresponding to the second medical image may be obtained based at least in part on the processing of the second medical image using the deformation relationship. The determining the deformation relationship and the registration network increases the convenience and accuracy for the physician to view the lesion region in the CT image and thus determine how the condition of the corresponding patient has changed.

FIG. 4 is a flowchart of a method for processing a medical image according to various embodiments of the present application.

At 410, a first medical image is obtained. In some embodiments, the obtaining the first medical image includes receiving the first medical image via an upload by a user. The first medical image may be uploaded by the user via a user interface that is provided to the user on a terminal. The first medical image may be obtained from a diagnostic equipment (e.g., an x-ray machine, a magnetic resonance imaging machine, a computerized tomography scan, etc.). The first medical image may be obtained from a data storage such as a server (e.g., a server that stores a database of medical images).

According to various embodiments, the user is a patient, a physician, or other care provider that is to view medical images in connection with providing medical services (e.g., diagnostic services, treatment services, etc.) to a patient. In some implementations, the user may be an individual having various other roles.

In some embodiments, the first medical image comprises a representation of a target organ. The target organ may be identified by a computer and/or an indication of the target organ may be provided by a user (e.g., via a user interface provided on a terminal). As an example, the target organ is an organ in the body of a patient (e.g., a human, an animal, a living being, etc.). Examples of a target organ include a brain, a heart, a lung, etc.

In some embodiments, the first medical image corresponds to the image of a target organ obtained with a medical imaging technology. The first medical image may be obtained directly from medical imaging technology or indirectly via accessing a storage on which the first medical image is stored (e.g., a storage on which the medical imaging technology stores the first medical image). As an example, the medical imaging technology may be, but is not limited to, X-rays, gamma rays, nuclear magnetic resonance, or ultrasound. Various medical imaging technologies may be used for capturing medical images corresponding to different target organs. The present application imposes no specific restrictions in this regard.

At 420, the first medical image is processed. According to various embodiments, the processing of the first medical image includes using a first machine learning model to process the first medical image. The first machine learning model may process the first medical image in connection with generating a classification result pertaining to the first medical image and/or generating (e.g., obtaining) a first image of a target region.

At 430, a classification result and/or a first image of a target region is obtained. In some embodiments, the classification result and/or the first image of the target region is obtained based at least in part on the processed first image. The first image of the target region may correspond to a particular region (e.g., a target region) within the first medical image. In some embodiments, the classification result and/or the first image of the target region corresponds to output(s) of the first machine learning model. The classification result and/or the first image of the target region may be stored in a data storage such as the data storage on which the first medical image is stored, etc. For example, the classification result may be stored on a network storage (e.g., in a database).

According to various embodiments, the first machine learning model is configured to obtain the first medical image, input the first medical image into an encoder network, obtain feature information pertaining to a target region, and separately input the feature information about the target region into a classification network and a decoder network to obtain the classification result and the first image.

In some embodiments, the classification result and/or the first image of the target region is obtained in a manner described above in connection with 230 and 240 of process 200 of FIG. 2. For example, 420 of process 400 may correspond to 220 of process 200.

At 440, a classification result and/or first image of the target region is provided. In some embodiments, the classification result and/or the first image of the target region is provided to a user via a user interface (e.g., displayed a display on a terminal such as terminal 100). The classification result and/or the first image may be displayed in a user interface of an application pertaining to an electronic medical record of the user. In some embodiments, providing the classification result and/or first image includes copying the corresponding files to an email or other electronic message and sending such email to a user (e.g., a patient, clinician, physician, etc.).

According to various embodiments, the first machine learning model is a trained model, or a reinforcement learning model. In embodiments of the present application, the example of a trained model is used for the purpose of illustration. The first machine learning model may employ an "encoder-decoder" structure according to which the output from the encoder network may correspond to an input to both the classification network and the decoder network, such that the classification network and the decoder network operate in parallel. In some embodiments, one or more of the encoder network and the decoder network use three-dimensional convolutional layers. As an example, both the encoder network and the decoder network use three-dimensional convolutional layers. For example, the first machine learning model may be a three-dimensional network model. In some embodiments, the encoder network employs a resnext50 network architecture. The decoder network may include an ASPP structure and upsampling layers, and the classification network may include a series of convolutional layers and global pooling layers. However, the encoder network, the decoder network, and the classification network are not limited to the foregoing.

According to various embodiments, an interface is provided to the user. The interface may be a graphical user interface that is displayed to the user via a terminal (e.g., a display device of, or operatively connected to, a terminal such as terminal 100). The graphical user interface may be an interface for an application pertaining to providing medical services, electronic medical records, etc.

FIG. 5 is a diagram of an interface used in connection with processing a medical image according to various embodiments of the present application.

According to various embodiments, interface 500 is implemented by terminal 100 of FIG. 1. Interface 500 may be implemented in connection with process 200 of FIG. 2, process 300 of FIG. 3, process 400 of FIG. 4, and/or process 600 of FIG. 6. Interface 500 may be invoked by, or used in connection with 440 of process 400 of FIG. 4.

As illustrated in FIG. 5, interface 500 may include an area 520 in which a medical image may be input (or selected) and/or a results display area 550. Interface 500 may include selectable element 530 and/or element 540 that upon selection of such invokes one or more functions or processes to be performed. Element 530 may correspond to a quantitative processing (e.g., to invoke a processing of the medical image). Element 540 may correspond to an image comparison (e.g., to invoke a comparison between two medical images).

In some embodiments, the medical image is obtained via user interaction with (e.g., user inputs with respect to) the area 520. As an example, interface 500 may include one or more selectable elements with respect to which a user may select a medical image or a function to be performed with respect to a medical image. In some embodiments, interface 500 includes element 510 that is configured to, in response to selection via a user input, facilitate a user to upload a medical image. As an example, in response to selection of element 510, another interface or window (e.g., a floating element) may be displayed that allows a user to browse a file system to select a desired medical image. As another example, in response to selection of element 510, another interface or window (e.g., a floating element) may be displayed that provides the use of a set of a plurality of images from which the user selects a desired medical image.

According to various embodiments, the user may select the medical image in need of uploading by clicking on "Upload Medical Image" (e.g., element 510), or the user may directly drag the medical image file to within the box bordered by the dashed line (e.g., area 520) to achieve the objective of uploading the medical image.

According to various embodiments, the classification result and/or the target region image is displayed in the results display area 550. As an example, the results display area 550 may be displayed on the right side for user viewing convenience. Interface 500 may display information pertaining to the patient and results display area 550 to assist the user (e.g., a physician or care provider) with conveniently accessing and viewing the medical image (e.g., a part of the medical image such as the target organ or the target region), and/or information pertaining to the quantitative analysis of the medical image.

Let us take the example of a user who is a physician for the purpose of illustration. After acquiring a patient's medical image, the physician may upload the medical image and view the classification result and target region displayed in the display area. The physician thus can determine the patient's condition and provide treatment suggestions based on the classification result and target region.

As an example, in the case that the user is a patient, after the user obtains the medical image for the patient, the patient may upload the medical image (e.g., to area 520 of the interface 500 of FIG. 5) and view the classification result and target region displayed in the display area (e.g., area 550 of the interface 500). Thus, the patient may gain a certain understanding of the patient's own condition and, on the basis thereof, may promptly go to the hospital for treatment. Interface 500 empowers patients to view results of the diagnostic test (e.g., CT scan) and to obtain certain information pertaining to a classification of an anomaly (or lack thereof) within the results of the diagnostic test. Similarly, care providers (e.g., physicians) may use interface 500 to quickly view results of a quantitative analysis (e.g., the classification results, image of the target region, and/or information pertaining to a deformation relationship over a set of medical images, etc.).

According to various embodiments, the first machine learning model is obtained (e.g., set and/or updated) by training a preset model by alternating between the use of multiple first training samples and multiple second training samples. Each first training sample may include a medical image containing the target organ, a classification label for the medical image, and label information for a target region in the medical image, and each second training sample may include a medical image containing the target organ and the classification label for the medical image. Process 200 may further include training the first machine learning model. The training the first machine learning model may include alternating between use of multiple first training samples and multiple second training samples to train a preset model and obtain a first machine learning model (or an updated first machine learning model). According to various embodiments, the first training samples include classification label(s), and the second training samples include the classification label(s) and the target region labels.

In some embodiments, in response to receiving a first request input by the user (e.g., to interface 500 of FIG. 5), the first medical image and a first proportion of the target region in the target organ is provided. The first medical image and/or the first proportion of the target region may be provided in the interface such as within area 550 of interface 500. The first proportion may be obtained based at least in part on the first image and a second image of the target organ. The second image may be obtained based at least in part on using a second machine learning model to process the first medical image.

According to various embodiments, an analysis of the medical image (or a set of medical images such as a series of medical images of a same organ over time) may be performed in response to a user request. As an example, the user may input to interface 500 the user request to perform the analysis of the medical image. As illustrated in FIG. 5, interface 500 may include elements 530 and/or 540 to which a user input may be input to select an analysis to be performed (e.g., and in response to which a function is invoked to perform the analysis of a selected medical image). The first request described above (e.g., in response to which the first medical image and a first proportion of the target region in the target organ is provided) may be a processing request input by the user who desires to view results of an analysis of at least part of the medical image (e.g., the quantitative result for the target region). For example, as illustrated in FIG. 5, interface 500 includes selectable element 530 that may be labeled (or otherwise correspond to) "quantitative processing." The user can invoke the "quantitative processing" based at least in part on clicking or otherwise selecting element 530. The first proportion for the target region may be displayed in the results display area (e.g., area 550) on interface 500. In some embodiments, in response to the user invoking the "quantitative processing," the first proportion for the target region is provided in area 550. Results of a quantitative analysis with respect to a particular medical image may be pre-stored (e.g., in advance of selection of element 530) and selection of element 530 may invoke an obtaining of the first proportion for the target region (or other information pertaining to the results of the quantitative analysis) such as from a storage on which the results of the quantitative analysis are pre-stored. The first proportion may correspond to the size of the target region as a proportion of the entire organ. As another example, the first proportion may be a ratio of a characteristic value pertaining to the target region in contrast to a characteristic value pertaining to the organ (e.g., the entire organ).

The second machine learning model may employ an "encoder-decoder" structure. In some embodiments, the "encoder-decoder" structure is obtained based at least in part on modifying networks such as UNet, PSPNet, or DeepLabV3+. The encoder network and decoder network in the second machine learning model may use three-dimensional convolutional layers so that the first machine learning model and the second machine learning model are three-dimensional networks.

In some embodiments, the method for processing the medical image includes obtaining a second request (e.g., to process the image). The second request may be input by the user to interface 500. In response to receiving the second request, a second medical image is obtained. For example, the second medical image may be obtained from a database of medical images, may be uploaded by the user via interface 500 (e.g., via selection or drag and drop to area 520 of interface 500), or otherwise selected by the user. The second medical image comprises the target organ. For example, the second medical image may include an image of the same organ comprised in the first medical image. The second medical image may be analyzed and a second proportion of the target region (e.g., in the target organ) may be determined. The second medical image and the second proportion of the target region in the target organ may be provided such as via display within results display area 550 of interface 500. According to various embodiments, the second proportion is obtained based at least in part on a third image of the target region in the second medical image and a fourth image of the target organ. The third image may be obtained based at least in part on a quantitative analysis of the second medical image. For example, the first machine learning model may be used to process the second medical image to obtain the third image. Similarly, the fourth image may be obtained based at least in part on a quantitative analysis of the second medical image. For example, the second machine learning model may be used to process the second medical image to obtain the fourth image.

According to various embodiments, an analysis of the medical image (or a set of medical images such as a series of medical images of a same organ over time) may be performed in response to a user request. As an example, the user may input to interface 500 the user request to perform the analysis of the medical image. As illustrated in FIG. 5, interface 500 may include elements 530 and/or 540 to which a user input may be input to select an analysis to be performed (e.g., and in response to which a function is invoked to perform the analysis of a selected medical image). The second request may correspond to a request to view the second medical image and/or to compare the second medical image to the first medical image. For example, the user may input a processing request. In some embodiments, the second request corresponds to a selection of element 540 corresponding to "image comparison." In response to selection of element 540, results of the image comparison are provided in results display area 550. The results of the image comparison may be generated in response to selection of element 540 (e.g., the analysis may be processed in response to the second request), or the results of the image comparison may be pre-stored before selection of element 540 and selection of element 540 may correspond to a retrieval of the results. In some embodiments, in response to selection of element 540, the second medical image and the second proportion for the target organ are displayed in the results display area 550.

According to various embodiments, the method for processing a medical image comprises providing (e.g., presenting, displaying, etc.) a registered image corresponding to the second medical image. The registered image may be based at least in part on an analysis of the first medical image and the second medical image and/or a difference between the first medical image and the second medical image. For example, the registered image may be obtained by processing the second medical image based at least in part on the deformation relationship between the first medical image and the second medical image. In some embodiments, the deformation relationship is obtained based at least in part on use of a third machine learning model to process the first medical image and the second medical image.

The third machine learning model may be a pre-built registration network. Medical images from different time periods may be input into the pre-built registration network, and the medical images from different time periods can be processed by a rigidity network having the same structure so as to determine the rigid body parameters of the medical images. The rigid body parameters may be processed using an affine grid network in connection with determining the deformation fields between the medical images (e.g., the deformation relationship between the medical images).

In some embodiments, the first medical image and the registered image are provided in the results display area 550 (e.g., at the same time). The first medical image and the registered image may be provided side-by-side within the results display area 550. The side-by-side display of the first medical image and the registered image provides a more convenient display to enable a user to assess (e.g., determine) how the target region has changed. In some embodiments, in addition to providing the first image and/or the registered image, quantitative and/or qualitative information pertaining to the images or the comparison of the images is provided (e.g., change in shape, size, color, identification of the organ, etc.). In some embodiments, the first proportion is provided on the first medical image, and the second proportion is provided on the registered image.

FIG. 6 is a flowchart of a method for processing a medical image according to various embodiments of the present application.

According to various embodiments, process 600 is implemented by terminal 100 of FIG. 1. Interface 500 of FIG. 5 and/or interface 700 of FIG. 7 may be implemented in connection with process 600.

At 610, a data source is obtained. The data source may be input by a user. For example, the user may provide one or more inputs to an interface to select or otherwise provide a data source.

In some embodiments, the data source corresponds to the first medical image. The obtaining the first medical image may include receiving the first medical image via an upload by a user. The first medical image may be obtained from a diagnostic equipment (e.g., an x-ray machine, a magnetic resonance imaging machine, a computerized tomography scan, etc.). The first medical image may be obtained from a data storage such as a server (e.g., a server that stores a database of medical images).

In some embodiments, the data source corresponds to a medical image (e.g., the first medical image). The medical image may comprise a representation of a target organ. The target organ may be identified by a computer and/or an indication of the target organ may be provided by a user (e.g., via a user interface provided on a terminal). As an example, the target organ is a human organ in the body of a patient (e.g., a human, an animal, a living being, etc.). Examples of a target organ include a brain, a heart, a lung, etc.

In some embodiments, the data source (e.g., first medical image) corresponds to the image of a target organ obtained with a medical imaging technology. The first medical image may be obtained directly from medical imaging technology or indirectly via accessing a storage on which the first medical image is stored (e.g., a storage on which the medical imaging technology stores the first medical image). As an example, the medical imaging technology may be, but is not limited to, X-rays, gamma rays, nuclear magnetic resonance, ultrasound, etc. Various medical imaging technologies may be used for capturing medical images corresponding to different target organs. The present application imposes no specific restrictions in this regard. Embodiments of the present application are explained using the example of a target organ that is a lung and a first medical image that is a CT (computed tomography) image.

At 620, a target process is selected. In some embodiments, the target process is a process by which the data source is to be analyzed (e.g., a selection of a quantities analysis to be performed on the first medical image). The target process may be selected based at least in part on one or more inputs by a user, such as an input to a user interface.

The target process may correspond to a processing algorithm. The target process may be selected from among multiple analysis processes (e.g., processing algorithms)

provided by the system. Different analysis processes (e.g., processing algorithms) may be provided in advance for medical images obtained with different imaging technologies. For example, a mapping of analysis processes to imaging technologies may be stored. A group of analysis processes corresponding to an imaging technology may be determined based on the mapping of analysis processes to imaging technologies. In response to a determination of an image technology used in connection with capturing the medical image (e.g., the data source), at least a subset of the group of analysis processes is provided to the user to enable the user to select the target process from among the subset of the group of analysis processes. The analysis processes may include existing processes for analyzing an image captured from a particular imaging technology. Different analysis processes may have different processing times, accuracies, etc.

At 630, the data source is processed based at least in part on the target process. For example, the target process is used to process the data source and to obtain a classification result for the data source and target data within the data source. In some embodiments, the target process includes invoking (e.g., calling) a first machine learning model to process the data source so as to obtain the classification result and the target data.

According to various embodiments, the first machine learning model is a trained model, or a reinforcement learning model. In embodiments of the present application, the example of a trained model is used for the purpose of illustration. The first machine learning model may use an "encoder-decoder" structure and may connect after the encoder network to a classification network which is parallel to the decoder network. For example, the network model may employ an "encoder-decoder" structure and the output from the encoder network may correspond to an input to both the classification network and the decoder network, such that the classification network and the decoder network operate in parallel. In some embodiments, one or more of the encoder network and the decoder network may make use of three-dimensional convolutional layers. As an example, both the encoder network and the decoder network use three-dimensional convolutional layers. For example, the first machine learning model may be a three-dimensional network model. In some embodiments, the encoder network employs a resnext50 network architecture. The decoder network may include an ASPP structure and upsampling layers, and the classification network may include a series of convolutional layers and global pooling layers. However, the encoder network, the decoder network, and the classification network are not limited to the foregoing.

At 640, classification result and target data are provided. In some embodiments, the classification result and the target data are provided via a graphical user interface of a terminal. The classification result and the target data may be provided to a user such as a patient, a physician or other care provider, etc.

In some embodiments, the user may be provided with an interface in connection with implementation of process 600 of FIG. 6.

FIG. 7 is a diagram of an interface used in connection with processing a medical image according to various embodiments of the present application.

According to various embodiments, interface 700 is implemented by terminal 100 of FIG. 1. Interface 700 may be implemented in connection with process 200 of FIG. 2, process 300 of FIG. 3, process 400 of FIG. 4, and/or process 600 of FIG. 6.

As illustrated in FIG. 7, interface 700 may include an area 710 (e.g., data source selection area) in which a data source is input (or selected) and/or a results display area 780. Interface 700 may also include an area 740 (e.g., a process selection area) within which a target process is selected (e.g., via one or more inputs).

Interface 700 may include selectable element 720 and/or element 730 with which one or more data sources may be selected. Selection of element 720 and/or 730 may provide to a user a set of medical images from which the data source is selected. As an example, in response to selection of element 720 and/or element 730, a file system may be accessed and/or provided to the user to navigate to a directory in which the data source is stored. In some embodiments, selection of the data source(s) includes a user dragging and dropping one or more medical images to the data source selection area (e.g., area 710) such as dragging a medical image over the element 720 and/or 730. Element 730 may correspond to an area in which (or an element with which) a quantitative processing is selected or determined (e.g., with which an input may be input to invoke a processing of the medical image). Element 740 may correspond to an area in which (or an element with which) an image comparison is selected or determined (e.g., with which an input may be input to invoke a comparison between two medical images).

According to various embodiments, interface 700 is provided to a user, and the user may select the to-be-processed data source from the data source selection area, and the storage location and specific type of the data source selected by the user may be displayed in this area. In response to selection of the data source, the user may then view in the process selection area at least one analysis process matching the data source. For example, in response to selection of the data source, a group of analysis processes corresponding to the data source may be determined. The determining the group of analysis processes corresponding to the data source may include determining an imaging technology associated with the data source, and determining the group of analysis processes based at least in part on the imaging technology. For example, a mapping of analysis processes to imaging technologies may be stored. A group of analysis processes corresponding to an imaging technology may be determined based on the mapping of analysis processes to imaging technologies. In response to a determination of an image technology used in connection with capturing the medical image (e.g., the data source), at least a subset of the group of analysis processes is provided to the user to enable the user to select the target process from among the subset of the group of analysis processes. The at least subset of the group of analysis processes may be provided to the user via the process selection area 740. In some embodiments, providing the at least subset of the group of analysis processes includes providing an indication of a name 760, a processing time, a location 750, a price 770, and other information relating to the corresponding analysis process(es). In some embodiments, the subset of the analysis processes is provided in a drop-down menu within the process selection area 740. In some embodiments, the subset of the analysis processes is provided with corresponding radial buttons. In response to selection of an analysis process via the drop-down menu or the radial button, the process selection area may be updated to reflect the corresponding name of the analysis process, a processing time, a price, and other information relating to the corresponding analysis process. The user may select the analysis process that is suited to the user's needs and thereby obtain the target process.

In response to the selection of the target process, the target process selected by the user is used to process the data source. Results from processing the data source (e.g., the medical image) may be provided in the results display area 780. In some embodiments, the data source and the results from the analysis thereof are provided in the results display area 780.

In some embodiments, the determining a target process selected by the user comprises: obtaining at least one analysis process corresponding to the data type of the data source; providing at least one analysis process (e.g., an indication of the analysis process); receiving a selection input by the user (e.g., to interface 700); and in response to the selection input from the user, determining the target process from among at least one analysis process based at least in part on the selection input.

Different analysis processes may be set up (e.g., defined) in advance for different types of data sources. For example, to use medical image classification and segmentation as an illustrative example, a traditional, features-based extraction method or a two-dimensional neural network image segmentation method may be provided. A processing method corresponding to the first machine learning model provided by embodiments of the present application may also be provided.

The selection input (e.g., corresponding to selection of the target process) may be a click signal generated by the user clicking on an analysis process. In some embodiments, in response to obtaining the click signal, the analysis process corresponding to the click signal (e.g., clicked on by the user based on the click position) may be determined, and the target process is correspondingly obtained.

In some embodiments, processing information for an analysis process is provided. The processing information includes at least one of the following: a processing device, a processing time, and a resource transfer amount. The user may make a selection of the target process based at least in part on the processing information.

Processing devices (e.g., used to perform the target process) may include local devices and cloud devices. The processing time may be the time needed for the analysis process to process the data source and produce the corresponding result for the user. The resource transfer amount may refer to the price to be paid to use the processing algorithm to process the data source.

For the convenience of different users, according to various embodiments, a user may be provided with selection options tailored for different analysis processes. For example, in the case of local devices versus cloud devices, local device analysis processes options are limited, and such analysis processes may have limited processing precision. Therefore, the price for a processing algorithm executed on a local device may be lower, and the price of a processing algorithm executed on a cloud device may be higher. As another example, the processing times of different analysis processes may vary. Thus, a corresponding price may be higher for analysis processes having shorter processing times.

According to various embodiments, the first machine learning model is obtained by training a preset model by alternating between use of multiple first training samples and multiple second training samples. Each first training sample may include a medical image comprising the target organ, a classification label for the medical image, and label information for the target region in the medical image. Each second training sample may include a medical image containing the target organ and the classification label for the medical image.

According to various embodiments, a terminal may implement at least part of process 200 of FIG. 2, process 300 of FIG. 3, process 400 of FIG. 4, and/or process 600 of FIG. 6. The terminal may implement interface 500 of FIG. 5 and/or interface 700 of FIG. 7. The terminal may be a computer terminal device in a group of computer terminals. In some embodiments, the terminal is a mobile terminal.

In some embodiments, the terminal is located on at least one network device among multiple network devices of a computer network.

The memory may be used to store software programs and modules (e.g., methods for processing a medical image), means, and program instructions/modules corresponding to data processing methods. By running software programs and modules stored in the memory, the processor executes various function applications and data processing (e.g., implements processing of the medical image and data processing described herein). The memory may comprise high-speed random access memory. The memory may further comprise non-volatile memory, such as one or more magnetic storage devices, flash memory, or other non-volatile solid-state memory. In some embodiments, the memory may further comprise memory that is remotely disposed relative to the processor. Such remote memory may be connected to the terminal via a network. Examples of the network described above include, but are not limited to, the Internet, corporate intranets, local area networks, mobile communication networks, and combinations thereof.

The processor, via the communication module, may call information and applications stored in the memory to execute the steps below: obtaining a first medical image comprising a target organ; and using a first machine learning model to process the first medical image and obtain a classification result for the first medical image and a first image of a target region in the first medical image. The first machine learning model is used in connection with obtaining the first medical image, inputting the first medical image into an encoder network, obtaining feature information about the target region, and separately inputting the feature information about the target region into a classification network and a decoder network to obtain the classification result and the first image.

Although various embodiments described above have been presented as a series of a combination of actions in order to simplify the description, the present application is not limited by the action sequences that are described. Some of the steps may make use of another sequence or be implemented simultaneously in accordance with the present application. Furthermore, certain ones of the actions and modules described in connection with the various embodiments are not necessarily required by the present application.

Through descriptions of the above implementations, various embodiments may be implemented using software and a general-use hardware platform. Hardware may be used to implement various embodiments, including process 200 of FIG. 2 and/or process 300 of FIG. 3. Computer software products used in connection with implementing various embodiments may be stored on storage media (such as ROM/RAM, magnetic disks, and optical disks) and include a certain number of instructions used to cause a piece of terminal equipment (which could be a mobile telephone, a computer, a server, or network equipment) to execute the methods described in the embodiments of the present application.

Please understand that, in several embodiments provided by the present application, the disclosed technical content may be implemented in other ways. The means embodiments described above are merely illustrative. For example, the division into said units is merely a division by logical function. When actually implemented, there may be other forms of division. For example, multiple units or components may be combined or integrated into another system, or some features might be omitted or not executed. Also, couplings or direct couplings or communication connections between things that are displayed or discussed may be through some interfaces. Indirect couplings or communication connections between units or modules may be electrical or otherwise.

Units described as separate components may or may not be physically separate, and components displayed as units may or may not be physical units. They can be located in one place, or they can be distributed across multiple network units. The embodiment schemes of the present embodiments can be realized by selecting part or all of the units in accordance with actual need.

In addition, each functional unit in each of the embodiments of the present application may be integrated into a processing unit, or each unit may have an independent physical existence. Or two or more units may be integrated into one unit. The integrated units described above may be implemented in the form of hardware, or they may be implemented in the form of software functional units.

If the integrated units are implemented in the form of software functional units and are sold or used as independent products, they may be stored in computer-readable media. With such an understanding, it becomes clear that the technical schemes of the present application, whether intrinsically or those portions that contribute to the prior art, or all or part of the technical schemes, may be embodied in the form of software products. These computer software products are stored in a storage medium and comprise some instructions for causing a computer device (which could be a personal computer, a server, or a network device) to execute all or some of the steps in the methods described by the various embodiments of the present application. The storage medium described above encompasses: USB flash drives, read-only memory (ROM), random access memory (RAM), mobile hard drives, magnetic or optical disks, or various other media that can store program code.

The above are merely preferred embodiments of the present application. Please note that persons with ordinary skill in the art could also make certain improvements and embellishments and that these improvements and embellishments should also be regarded as being within the protective scope of the present application, so long as they do not depart from the principles of the present application.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
receiving, by one or more processors, a first image based at least in part on an input from a user;
determining, by the one or more processors, a target process to be used in connection with analyzing the first image, the target process being determined based at least in part on a selection input by the user;
processing, by the one or more processors, the first image based at least in part on the target process, wherein:
a classification result for the first image, target data within the first image, and a target organ image, and a deformation relationship between the first image and a second image are obtained based at least in part on the processing of the first image; and
the target process is configured to call:
a first machine learning model in connection with processing the first image to obtain the classification result and the target data;
a second machine learning model in connection with processing the first image to obtain the target organ image;
a third machine learning model in connection with processing the first image and a second image to obtain the deformation relationship between the first image and a second image; and
the third machine learning model is configured to:
input the first image and the second image separately into at least two rigidity networks;
obtain a first rigid body parameter of the first image and a second rigid body parameter of the second image;
input the first rigid body parameter and the second rigid body parameter into an affine grid network; and
obtain the deformation relationship based at least in part on a processing of the affine grid network using the first rigid body parameter and the second rigid body parameter;
obtaining proportion data, comprising:
obtaining a registered image corresponding to the second image based on a processing of the second image, wherein the processing of the second image is based at least in part on the deformation relationship;
obtaining the third image and the fourth image based at least in part on a separate processing of the registered image based at least in part on the first machine learning model and the second machine learning model;
obtaining a first proportion of the target region in the target organ based at least in part on the first image and the second image; and
obtaining a second proportion of the target region in the target organ, the second proportion being obtained based at least in part on the third image and the fourth image; and
outputting, by the one or more processors, the classification result, the target data, the target organ image, the proportion data, and the deformation relationship.

2. The method of claim 1, wherein determining a target process comprises:
obtaining at least one analysis process corresponding to a data type of the first image;
outputting, on a user interface, information pertaining to the at least one analysis process;
receiving, by the one or more processors, a selection input by the user, the selection input corresponding to a selection of an analysis process; and
in response to receiving the selection input, determining, by the one or more processors, the target process from among the at least one analysis processes based at least in part on the selection input.

3. The method of claim 2, further comprising:
outputting, by the one or more processors, processing information pertaining to the target process, wherein the processing information includes at least one of the following: a processing device, a processing time, and a resource transfer amount.

4. The method of claim 1, wherein:
the first machine learning model is obtained by training a preset model based at least in part on an alternating between use of multiple first training samples and multiple second training samples;
each first training sample comprises data, a classification label for the data, and label information for target data within the data; and
each second training sample comprises data and a classification label for the data.

5. A method, comprising:
obtaining, by one or more processors, a first medical image, wherein the first medical image includes a representation of a target organ; and
processing, by the one or more processors, the first medical image based at least in part on a first machine learning model, wherein:
    a classification result associated with the first medical image, a first image of a target region in the first medical image, a target organ image, and a deformation relationship between the first medical image and a second medical image are obtained based at least in part on the processing of the first medical image;
    the classification result and the first image of the target region are obtained using the first machine learning model, the first machine learning model being configured to:
        obtain the first medical image and input the first medical image into an encoder network;
        obtain feature information associated with the target region;
        separately input the feature information associated with the target region into a classification network and a decoder network; and
        obtain the classification result and the first image of the target region based at least in part on a processing of the feature information by the classification network and the decoder network;
    the target organ image is obtained using a second machine learning model;
    the deformation relationship between the first image and the second medical image is obtained using a third machine learning model; and
    the third machine learning model is configured to:
        input the first medical image and the second medical image separately into at least two rigidity networks;
        obtain a first rigid body parameter of the first medical image and a second rigid body parameter of the second medical image;
        input the first rigid body parameter and the second rigid body parameter into an affine grid network; and
        obtain the deformation relationship based at least in part on a processing of the affine grid network using the first rigid body parameter and the second rigid body parameter;
obtaining proportion data, comprising:
    obtaining a registered image corresponding to the second medical image based on a processing of the second medical image, wherein the processing of the second medical image is based at least in part on the deformation relationship;
    obtaining the third image and the fourth image based at least in part on a separate processing of the registered image based at least in part on the first machine learning model and the second machine learning model;
    obtaining a first proportion of the target region in the target organ based at least in part on the first image and the second image; and
    obtaining a second proportion of the target region in the target organ, the second proportion being obtained based at least in part on the third image and the fourth image;
storing the classification result, the target data, the target organ image, the proportion data, and the deformation relationship; and
configuring a user interface to present the classification result based at least in part on one or more of the classification result, the target data, the target organ image, the proportion data, and the deformation relationship.

6. The method of claim 5, further comprising:
obtaining multiple first training samples and multiple second training samples, wherein:
    each first training sample comprises a medical image comprising a representation of a target organ, a classification label for the medical image, and label information for the target region in the medical image; and
    each second training sample comprises a medical image comprising a representation of the target organ and the classification label for the medical image; and
alternating between use of the multiple first training samples and the multiple second training samples to train a preset model and to obtain the first machine learning model.

7. The method of claim 5, further comprising:
the processing of the first medical image using the second machine learning model is performed after the first image of the target region is obtained; and
the second machine learning model is configured to:
    obtain the first medical image;
    input the first medical image into an encoder network;
    obtain feature information pertaining to the target organ;
    input the feature information pertaining to the target organ into a decoder network; and
    obtain the target organ image based at least in part on a processing of the feature information by the decoder network; and
obtaining a first proportion of the target region in the target organ based at least in part on the first medical image and the second medical image.

8. The method of claim 7, wherein the first proportion is determined based at least in part on a difference or change between the first image and the second image.

9. The method of claim 7, further comprising:
obtaining, by the one or more processors, the second medical image comprising a representation of the target organ;
processing, by the one or more processors, the second medical image based at least in part on the first machine learning model, wherein the third image of the target region in the second medical image is obtained based at least in part on the processing of the second medical image using the first machine learning model; and processing, by the one or more processors, the second medical image based at least in part on the second machine learning model, wherein the fourth image of the target organ is obtained based at least in part on the processing of the second medical image using the second machine learning model.

10. The method of claim 7, wherein the encoder network in the second machine learning model and the encoder network in the first machine learning model share weighting parameters.

11. The method of claim 7, wherein the encoder network and the decoder network both use three-dimensional convolutional layers.

12. A medical image processing method, comprising:
receiving, by one or more processors, a first medical image comprising a representation of a target organ, wherein the first medical image is uploaded via an interface provided by a terminal; and
outputting, by the one or more processors, (i) a classification result for the first medical image and a first image of a target region in the first medical image, (ii) a target organ image, (iii) target data, (iv) proportion data, and (v) a deformation relationship between the first medical image and a second medical image;
wherein:
the classification result and the first image are obtained based at least in part on a processing of the first medical image using a first machine learning model;
the target organ image is obtained based at least in part on processing the first medical image using a second machine learning model;
the deformation relationship is obtained based at least in part on processing the first medical image using a third machine learning model;
the third machine learning model is configured to:
input the first image and the second image separately into at least two rigidity networks;
obtain a first rigid body parameter of the first image and a second rigid body parameter of the second image;
input the first rigid body parameter and the second rigid body parameter into an affine grid network; and
obtain the deformation relationship based at least in part on a processing of the affine grid network using the first rigid body parameter and the second rigid body parameter; and
the proportion data is obtained based at least in part on:
obtaining a registered image corresponding to the second medical image based on a processing of the second medical image, wherein the processing of the second medical image is based at least in part on the deformation relationship;
obtaining the third image and the fourth image based at least in part on a separate processing of the registered image based at least in part on the first machine learning model and the second machine learning model;
obtaining a first proportion of the target region in the target organ based at least in part on the first image and the second image; and
obtaining a second proportion of the target region in the target organ, the second proportion being obtained based at least in part on the third image and the fourth image.

13. The method of claim 12, further comprising
receiving, by the one or more processors, a first request, wherein the first request is input to the terminal via the interface; and
in response to receiving the first request, outputting, by the one or more processors, the first medical image and the first proportion, wherein the first proportion comprises a first proportion of the target region in the target organ.

14. The method of claim 13, further comprising:
receiving, by the one or more processors, a second request, wherein the second request is input to the terminal via the interface;
in response to receiving the second request, outputting, by the one or more processors, the second medical image and the second proportion, wherein the second proportion comprises a second proportion of the target region in the target organ.

15. The method of claim 14, wherein:
the first medical image and the registered image are output side-by-side on the interface;
the first proportion is presented on the first medical image; and
the second proportion is presented on the registered image.

16. A computer program product, the computer program product being embodied in a non-transitory computer readable storage medium and comprising computer instructions for:
receiving, by one or more processors, a first image based at least in part on an input from a user;
determining, by the one or more processors, a target process to be used in connection with analyzing the first image, the target process being determined based at least in part on a selection input by the user;
processing, by the one or more processors, the first image based at least in part on the target process, wherein:
a classification result for the first image, target data within the first image a target organ image, and a deformation relationship between the first image and a second image are obtained based at least in part on the processing of the first image; and
the target process is configured to call:
a first machine learning model in connection with processing the first image to obtain the classification result and the target data; a second machine learning model in connection with processing the first image to obtain the target organ image; and
a third machine learning model in connection with processing the first image to obtain the deformation relationship between the first image and a second image; and
the third machine learning model is configured to:
input the first image and the second image separately into at least two rigidity networks;
obtain a first rigid body parameter of the first image and a second rigid body parameter of the second image;
input the first rigid body parameter and the second rigid body parameter into an affine grid network; and
obtain the deformation relationship based at least in part on a processing of the affine grid network using the first rigid body parameter and the second rigid body parameter; and obtaining proportion data, comprising:
  obtaining a registered image corresponding to the second image based on a processing of the second image, wherein the processing of the second image is based at least in part on the deformation relationship;
  obtaining the third image and the fourth image based at least in part on a separate processing of the registered image based at least in part on the first machine learning model and the second machine learning model;
  obtaining a first proportion of the target region in the target organ based at least in part on the first image and the second image; and
  obtaining a second proportion of the target region in the target organ, the second proportion being obtained based at least in part on the third image and the fourth image; and
outputting, by the one or more processors, the classification result, the target data, the target organ image, and the deformation relationship.

17. A computer program product, the computer program product being embodied in a non-transitory computer readable storage medium and comprising computer instructions for:
  obtaining, by one or more processors, a first medical image, wherein the first medical image includes a representation of a target organ;
  processing, by the one or more processors, the first medical image based at least in part on a first machine learning model, wherein:
    a classification result associated with the first medical image, a first image of a target region in the first medical image, a target organ image, and a deformation relationship between the first medical image and a second medical image are obtained based at least in part on the processing of the first medical image;
    the classification result and the first image of the target region are obtained using the first machine learning model, the first machine learning model being configured to:
      obtain the first medical image and input the first medical image into an encoder network;
      obtain feature information associated with the target region;
      separately input the feature information associated with the target region into a classification network and a decoder network; and
      obtain the classification result and the first image of the target region based at least in part on a processing of the feature information by the classification network and the decoder network;
    the target organ image is obtained using a second machine learning model;
    the deformation relationship between the first image and the second medical image is obtained using a third machine learning model; and
    the third machine learning model is configured to:
      input the first medical image and the second medical image separately into at least two rigidity networks;
      obtain a first rigid body parameter of the first medical image and a second rigid body parameter of the second medical image;
      input the first rigid body parameter and the second rigid body parameter into an affine grid network; and
      obtain the deformation relationship based at least in part on a processing of the affine grid network using the first rigid body parameter and the second rigid body parameter;
  obtaining proportion data, comprising:
    obtaining a registered image corresponding to the second medical image based on a processing of the second medical image, wherein the processing of the second medical image is based at least in part on the deformation relationship;
    obtaining the third image and the fourth image based at least in part on a separate processing of the registered image based at least in part on the first machine learning model and the second machine learning model;
    obtaining a first proportion of the target region in the target organ based at least in part on the first image and the second image; and
    obtaining a second proportion of the target region in the target organ, the second proportion being obtained based at least in part on the third image and the fourth image;
  storing the classification result, the target data, the target organ image, the proportion data, and the deformation relationship; and
  configuring a user interface to present the classification result based at least in part on one or more of the classification result, the target data, the target organ image, the proportion data, and the deformation relationship.

18. A medical image processing system, comprising:
one or more processors configured to:
  obtain a first medical image, wherein the first medical image includes a representation of a target organ;
  process the first medical image based at least in part on a first machine learning model, wherein:
    a classification result associated with the first medical image, a first image of a target region in the first medical image, a target organ image, and a deformation relationship between the first medical image and a second medical image are obtained based at least in part on the processing of the first medical image;
    the classification result and the first image of the target region are obtained using the first machine learning model, the first machine learning model being configured to:
      obtain the first medical image and input the first medical image into an encoder network;
      obtain feature information associated with the target region;
      separately input the feature information associated with the target region into a classification network and a decoder network; and
      obtain the classification result and the first image of the target region based at least in part on a processing of the feature information by the classification network and the decoder network;
    the target organ image is obtained using a second machine learning model;
    the deformation relationship between the first image and the second medical image is obtained using a third machine learning model;

the third machine learning model is configured to:
  input the first medical image and the second medical image separately into at least two rigidity networks;
  obtain a first rigid body parameter of the first medical image and a second rigid body parameter of the second medical image;
  input the first rigid body parameter and the second rigid body parameter into an affine grid network; and
  obtain the deformation relationship based at least in part on a processing of the affine grid network using the first rigid body parameter and the second rigid body parameter;
obtain proportion data, wherein obtaining the proportion data comprises:
  obtaining a registered image corresponding to the second medical image based on a processing of the second medical image, wherein the processing of the second medical image is based at least in part on the deformation relationship;
  obtaining the third image and the fourth image based at least in part on a separate processing of the registered image based at least in part on the first machine learning model and the second machine learning model;
  obtaining a first proportion of the target region in the target organ based at least in part on the first image and the second image; and
  obtaining a second proportion of the target region in the target organ, the second proportion being obtained based at least in part on the third image and the fourth image;
store the classification result, the target data, the target organ image, the proportion data, and the deformation relationship;
configure a user interface to present the classification result based at least in part on one or more of the classification result, the target data, the target organ image, the proportion data, and the deformation relationship; and
one or more memories coupled to the one or more processors, configured to provide the one or more processors with instructions.

* * * * *